United States Patent
Imaizumi (10) Patent No.: US 9,138,136 B2
(45) Date of Patent: Sep. 22, 2015

(54) SCANNING ENDOSCOPE APPARATUS, IMAGE PROCESSING APPARATUS AND OPERATION METHOD OF IMAGE PROCESSING APPARATUS

(71) Applicant: OLYMPUS MEDICAL SYSTEMS CORP., Tokyo (JP)

(72) Inventor: Katsuichi Imaizumi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 89 days.

(21) Appl. No.: 14/135,909

(22) Filed: Dec. 20, 2013

(65) Prior Publication Data
US 2014/0180011 A1   Jun. 26, 2014

Related U.S. Application Data

(63) Continuation of application No. PCT/JP2013/062703, filed on May 1, 2013.

(30) Foreign Application Priority Data

Aug. 7, 2012   (JP) ................................. 2012-175245

(51) Int. Cl.
*A61B 1/06* (2006.01)
*A61B 1/00* (2006.01)

(52) U.S. Cl.
CPC ............ *A61B 1/0676* (2013.01); *A61B 1/00009* (2013.01); *A61B 1/00172* (2013.01)

(58) Field of Classification Search
CPC ............ A61B 1/00; A61B 1/04; A61B 1/043; A61B 1/00004; A61B 1/00009; A61B 1/06; A61B 1/0638; A61B 1/0646; A61B 1/0661; A61B 5/0059; A61B 5/0071; A61B 5/0062; A61B 18/20; A61B 18/22; A61B 2017/00022; A61B 2017/00057; A61B 2017/00061; A61B 2017/00066

USPC ........ 600/104, 106, 107, 108, 109, 118, 160, 600/178, 180, 181, 182
See application file for complete search history.

(56) References Cited

U.S. PATENT DOCUMENTS 4,418,689 A * 12/1983 Kanazawa ..................... 600/108
5,309,895 A    5/1994 Yabe
(Continued)

FOREIGN PATENT DOCUMENTS

JP    05-095899 A    4/1993
JP    09-248281 A    9/1997
(Continued)

*Primary Examiner* — Anhtuan T Nguyen
*Assistant Examiner* — William Chou
(74) *Attorney, Agent, or Firm* — Scully, Scott, Murphy & Presser, PC (57) ABSTRACT

A scanning endoscope apparatus includes: a light source section that emits illuminating light; an optical fiber that guides and applies the illuminating light from a distal end, the illuminating light having directionality; a drive element and a scanning drive section that scan the distal end of the optical fiber; a light detecting section that detects light from a subject; a shutter and an intermittent light output control section that controls a light application period and an interruption period for the illuminating light; an extrinsic light component removal section that outputs a result of an average value of a plurality of light detection results obtained in the interruption period being subtracted from each of a plurality of light detection results obtained in the light application period; and an image processing section that forms image information for display, based on the result outputted by the extrinsic light component removal section.

2 Claims, 7 Drawing Sheets

(56) References Cited

U.S. PATENT DOCUMENTS

| | | | |
|---|---|---|---|
| 5,749,830 A * | 5/1998 | Kaneko et al. | 600/160 |
| 5,954,633 A * | 9/1999 | Hirata | 600/108 |
| 6,167,297 A * | 12/2000 | Benaron | 600/431 |
| 6,537,211 B1 * | 3/2003 | Wang et al. | 600/178 |
| 8,259,167 B2 * | 9/2012 | Ishiwata et al. | 348/65 |
| 8,974,378 B2 * | 3/2015 | Imaizumi et al. | 600/178 |
| 2002/0105505 A1 * | 8/2002 | Sendai | 345/204 |
| 2002/0161282 A1 * | 10/2002 | Fulghum | 600/160 |
| 2008/0221388 A1 * | 9/2008 | Seibel et al. | 600/109 |
| 2012/0323072 A1 * | 12/2012 | Ishihara | 600/109 |

FOREIGN PATENT DOCUMENTS

| | | |
|---|---|---|
| JP | 10-276976 A | 10/1998 |
| JP | 2002-354346 A | 12/2002 |
| JP | 2010-643497 A | 3/2010 |
| JP | 2011-019706 A | 2/2011 |
| JP | 2011-045461 A | 3/2011 |

\* cited by examiner

SCANNING ENDOSCOPE APPARATUS, IMAGE PROCESSING APPARATUS AND OPERATION METHOD OF IMAGE PROCESSING APPARATUS

CROSS REFERENCE TO RELATED APPLICATION

This application is a continuation application of PCT/JP2013/062703 filed on May 1, 2013 and claims benefit of Japanese Application No. 2012-175245 filed in Japan on Aug. 7, 2012, the entire contents of which are incorporated herein by this reference.

BACKGROUND OF THE INVENTION

1. Field of the Invention

The present invention relates to a scanning endoscope apparatus that scans directional illuminating light to obtain an image of a subject, an image processing apparatus that processes the image obtained by the scanning endoscope apparatus, and a method of operation of the image processing apparatus.

2. Description of the Related Art

Conventionally, scanning endoscope apparatuses that apply illuminating light to a subject in such a manner that the illuminating light has directionality, and receive reflected light while scanning a direction of application of the illuminating light to obtain an image of the subject have been proposed.

For example, Japanese Patent Application Laid-Open Publication No. 2011-19706 describes a medical observation system including a medical probe that scans laser light to observe an object, a laser light source that supplies the laser light to the medical probe, determination means for determining whether or not the medical probe is in a predetermined state, and control means for controlling an amount of laser light outputted from the laser light source based on a result of the determination by the determination means. It is disclosed that such configuration enables the amount of laser light to be limited to a safe level in a situation in which the laser light may enter the eyes of a surgeon or the like.

Also, in a technique described in Japanese Patent Application Laid-Open Publication No. 9-248281, an endoscope spectral apparatus (3) is used in combination with an electronic endoscope apparatus (2). The electronic endoscope apparatus (2) includes an electronic endoscope (4) including image pickup means, observation light illumination means (5) for supplying illuminating light for observation to the electronic endoscope (4), and a signal processing section (6) that processes a signal from the image pickup means. The endoscope spectral apparatus (3) includes measurement light illumination means (9) for applying measurement light, spectral means for performing spectrometric measurement (10), a measurement probe (11) to be inserted into a channel in the electronic endoscope (4), and timing control means (12) for controlling an operation timing of the spectral means (10). The measurement probe (11) includes a fiber bundle for illumination and a fiber bundle for light reception, and the fiber bundle for illumination is connected to the measurement light illumination means (9) and the fiber bundle for light reception is connected to the spectral means (10), respectively. Measurement light from the measurement light illumination means (9) is guided by the fiber bundle for illumination and applied to the inside of a living body (30). Light reflected from the inside of the living body (30) is received by the fiber bundle for light reception and guided to the spectral means (10). A signal synchronized with light blocking periods in which observation light is blocked is inputted to the timing control means (12) from the electronic endoscope apparatus (2). Then, the timing control means (12) makes the spectral means (10) perform spectral measurement, based on a measurement control signal synchronized with the light blocking periods. Consequently, it is disclosed that highly-accurate spectral measurement data that is not affected by observation light can be obtained with almost no change in specifications of the endoscope apparatus (2).

Such scanning endoscope apparatus is configured so that a direction of an output end of an optical fiber that guides illuminating light can be varied, and the direction of the output end of the optical fiber is varied as time passes, whereby illuminating light is scanned. On the other hand, a configuration that receives light from a subject is made so that, for example, all of light from within an illuminating light scanning range can be received.

Accordingly, information indicating from which direction received light has come (that is, from which part of a subject the received light has come) is not contained in a signal generated by the received light. Therefore, an endoscopic image is formed assuming that the received light is return light from a part of the subject to which the output light is applied.

With the above-mentioned configuration of the conventional scanning endoscope apparatus, an image of a subject can accurately be formed if there is no light other than return light from the subject within the light reception range; however, if there is extrinsic light other than return light (light that is not return light of illuminating light outputted from the optical fiber, for example, light generated by a treatment instrument for performing treatment of a subject, the treatment being accompanied by light emission, such as an electrosurgical knife or a therapeutic laser), detected light contains the extrinsic light. In other words, detected light is a sum of the return light from the subject to which the illuminating light has been applied and the extrinsic light received regardless of in which direction the illuminating light is applied.

SUMMARY OF THE INVENTION

A scanning endoscope apparatus according to an aspect of the present invention includes: a light source section that emits illuminating light; a light guiding section that guides and applies the illuminating light to a subject from a distal end in such a manner that the illuminating light has directionality; a scanning section that performs scanning in which a direction of the distal end of the light guiding section is varied; a light detecting section that detects light from the subject; an illumination control section that controls a light application period in which the illuminating light is applied from the distal end of the light guiding section and an interruption period in which the application of the illuminating light from the distal end of the light guiding section is interrupted; a removal section that outputs a result of an average value of a plurality of detection results obtained by the light detecting section in the interruption period being subtracted from each of a plurality of detection results each obtained according to the direction of the distal end varied by the scanning section in the light application period; and an image processing section that forms image information to be outputted to a display section that displays an image, based on the result outputted by the removal section.

A scanning endoscope apparatus according to another aspect of the present invention includes: a light source section that emits illuminating light; a light guiding section that guides and applies the illuminating light to a subject from a distal end in such a manner that the illuminating light has directionality; a scanning section that performs scanning in which a direction of the distal end of the light guiding section is varied; a first light detecting section that detects light in a wavelength band of the illuminating light; a second light detecting section that does not detect light in the wavelength band of the illuminating light, but detects light in a wavelength band other than the wavelength band of the illuminating light; an illumination control section that controls a light application period in which the illuminating light is applied from the distal end of the light guiding section and an interruption period in which the application of the illuminating light from the distal end of the light guiding section is interrupted; a removal section that corrects a result of detection by the second light detecting section in the light application period, based on a ratio of a result of detection by the first light detecting section relative to a result of detection by the second light detecting section in the interruption period to estimate an extrinsic light component contained in the result of detection by the first light detecting section in the light application period, and removes the estimated extrinsic light component to extract a return light component of the illuminating light from the subject; and an image processing section that forms image information to be outputted to a display section that displays an image, based on the return light component extracted by the removal section.

An image processing apparatus according to an aspect of the present invention is an image processing apparatus for processing an image obtained by a scanning endoscope apparatus, the scanning endoscope apparatus including a light source section that emits illuminating light, a light guiding section that guides and applies the illuminating light to a subject from a distal end in such a manner that the illuminating light has directionality, a scanning section that performs scanning in which a direction of the distal end of the light guiding section is varied, a light detecting section that detects light from the subject, and an illumination control section that controls a light application period in which the illuminating light is applied from the distal end of the light guiding section and an interruption period in which the application of the illuminating light from the distal end of the light guiding section is interrupted, the image processing apparatus including: a removal section that outputs a result of an average value of a plurality of detection results obtained by the light detecting section in the interruption period being subtracted from each of a plurality of detection results each obtained according to the direction of the distal end varied by the scanning section in the light application period; and an image processing section that forms image information to be outputted to a display section that displays an image, based on the result outputted by the removal section.

A method of operation of an image processing apparatus according to an aspect of the present invention is a method of operation of an image processing apparatus for processing an image obtained by a scanning endoscope apparatus, the scanning endoscope apparatus including a light source section that emits illuminating light, a light guiding section that guides and applies the illuminating light to a subject from a distal end in such a manner that the illuminating light has directionality, a scanning section that performs scanning in which a direction of the distal end of the light guiding section is varied, a light detecting section that detects light from the subject, and an illumination control section that controls a light application period in which the illuminating light is applied from the distal end of the light guiding section and an interruption period in which the application of the illuminating light from the distal end of the light guiding section is interrupted, wherein a removal section outputs a result of an average value of a plurality of detection results obtained by the light detecting section in the interruption period being subtracted from each of a plurality of detection results each obtained from the light detecting section according to the direction of the distal end varied by the scanning section in the light application period; and wherein an image processing section forms image information to be outputted to a display section that displays an image, based on the result outputted from the removal section.

DETAILED DESCRIPTION OF THE PREFERRED EMBODIMENTS

Embodiments of the present invention will be described below with reference to the drawings.

[Embodiment 1]

Figure 1:
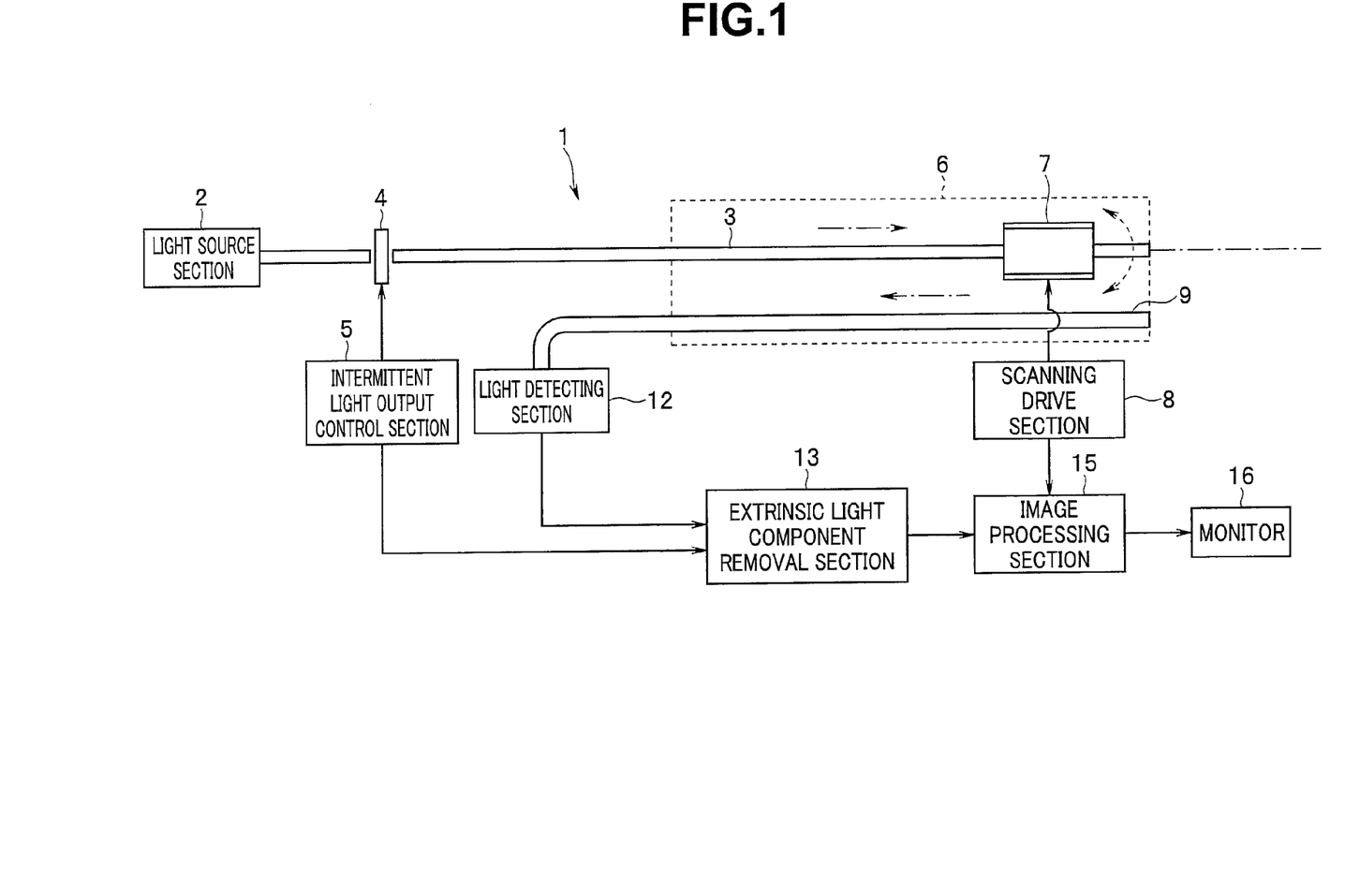
FIG. 1 is a diagram illustrating an example configuration of a scanning endoscope apparatus according to Embodiment 1 of the present invention.

FIGS. 1 to 6 illustrate Embodiment 1 of the present invention, and FIG. 1 is a diagram illustrating an example configuration of a scanning endoscope apparatus 1.

The scanning endoscope apparatus 1 according to the present embodiment includes a light source section 2, an optical fiber 3, a shutter 4, an intermittent light output control section 5, an endoscope 6, a drive element 7, a scanning drive section 8, an optical fiber bundle 9, a light detecting section 12, an extrinsic light component removal section 13, an image processing section 15 and a monitor 16.

The light source section 2 is one that emits illuminating light, and is, for example, one that emits illuminating light of a plurality of colors, more specifically, one that includes a red light emitting laser that emits red (R) narrow-band light, a green light emitting laser that emits green (G) narrow-band light and a blue light emitting laser that emits blue (B) narrow-band light, and thereby emits color illuminating light. Here, the lasers are used as light sources because the lasers emit coherent light, enabling provision of a less-diffused (that is, highly-directional) light beam. Note that, although it is assumed that the light source section 2 is one that emits color illuminating light containing three color components of RGB, it should be understood that if it is sufficient to obtain a monochrome image, one that emits monochrome illuminating light may be employed. Alternatively, one that emits light such as ultraviolet light, infrared light or light for narrow-band observation (narrow band imaging: NBI) may be employed.

The optical fiber 3 is a light guiding section that guides the illuminating light emitted from the light source section 2, and applies the illuminating light to a subject from a distal end in such a manner that the illuminating light has directionality, and in order to suppress diffusion of output light, for example, a single-mode optical fiber is used for the optical fiber 3. The distal end of the optical fiber 3 is arranged at a distal end of the endoscope 6. The applied illuminating light is reflected by the subject and thereby turns to return light, which enters a distal end of the optical fiber bundle 9.

The shutter 4 and the intermittent light output control section 5 form an illumination control section that controls light application periods in which illuminating light is applied from the distal end of the optical fiber 3 and interruption periods in which the application of the illuminating light from the distal end of the optical fiber 3 is interrupted, with a predetermined cycle. In other words, the shutter 4 is arranged on a route of light guide by the optical fiber 3 and provides a switch for selecting whether the illuminating light emitted from the light source section 2 is guided to the distal end side of the optical fiber 3 or interrupted. Also, the intermittent light output control section 5 drives the shutter 4 to control the light application periods and the interruption periods.

The endoscope 6 is to be inserted into a subject, the optical fiber 3 and the optical fiber bundle 9 are inserted inside the endoscope 6, and the drive element 7 is also disposed in the endoscope 6.

The drive element 7 and the scanning drive section 8 form a scanning section that performs scanning in which a direction of the distal end of the optical fiber 3 is varied. The drive element 7 is a drive source that moves the distal end of the optical fiber 3, and, for example, includes a piezo element. Also, the scanning drive section 8 is a driver that controls a drive current supplied to the drive element 7.

The optical fiber bundle 9 whose distal end is arranged at the distal end of the endoscope 6 receives the return light from the subject and guides the return light to the proximal end side. The optical fiber bundle 9 performs light reception with wide directionality so that the optical fiber bundle 9 can receive light from all directions within a range of scanning of the optical fiber 3.

The light detecting section 12 detects the return light guided via the optical fiber bundle 9 to detect light from the range of scanning of the distal end of the optical fiber 3 by the drive element 7 and the scanning drive section 8 in such a manner that such detection has wide directionality.

The extrinsic light component removal section 13 removes extrinsic light components, which can be obtained in such a manner as described later based on results of detection by the light detecting section 12 in an interruption period, from a result of detection by the light detecting section 12 in a light application period, to extract return light components of illuminating light from the subject.

The image processing section 15 calculates from which direction the return light components extracted by the extrinsic light component removal section 13 have come, based on information on the direction of the distal end of the optical fiber 3 from the scanning drive section 8, to form an image and outputs the image to the monitor 16.

The monitor 16 displays the image formed by the image processing section 15.

Figure 2:
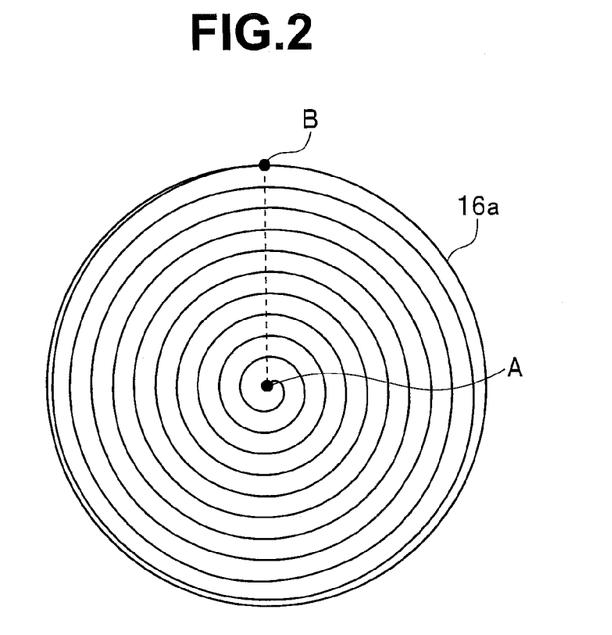
FIG. 2 is a diagram illustrating a manner of light scanning by the scanning endoscope apparatus according to Embodiment 1.

Next, FIG. 2 is a diagram illustrating a manner of light scanning by the scanning endoscope apparatus 1.

Scanning of the distal end of the optical fiber 3 by the drive element 7 and the scanning drive section 8 is performed, for example, as illustrated in FIG. 2.

In other words, variation of the direction is started from a center point A of an observation view field 16a, the direction of the distal end of the optical fiber 3 is varied along a spiral route to make the distal end of the optical fiber 3 reach a farthest point B, which is farthest from the center. Subsequently, operation similar to the above may be performed after the application of the illuminating light to the subject is turned off and the direction of the distal end of the optical fiber 3 is returned from the farthest point B to the center point A, or the direction of the distal end of the optical fiber 3 may be returned to the center point A by following the spiral route from the farthest point B in a reverse direction, or another method may be employed. For convenience, in the present embodiment, the method in which the direction of the distal end of the optical fiber 3 is returned to the center point A by following the spiral route from the farthest point B in the reverse direction.

As described above, the light detecting section 12 has wide directionality to receive light so that the light detecting section 12 can receive all of light from the scanning range such as illustrated in FIG. 2. Accordingly, from which point in the scanning range light detected by the light detecting section 12 has come cannot be determined from a result of the detection by the light detecting section 12 alone.

Therefore, the image processing section 15 receives information on the direction of the distal end of the scanning optical fiber 3 (that is, information on a direction of application of the illuminating light) from the scanning drive section 8, and estimates that the return light components extracted by the extrinsic light component removal section 13 are of light from a part of the subject that is positioned in the direction of the distal end of the optical fiber 3, and maps the return light components in the estimated position to form an image.

Figure 3:
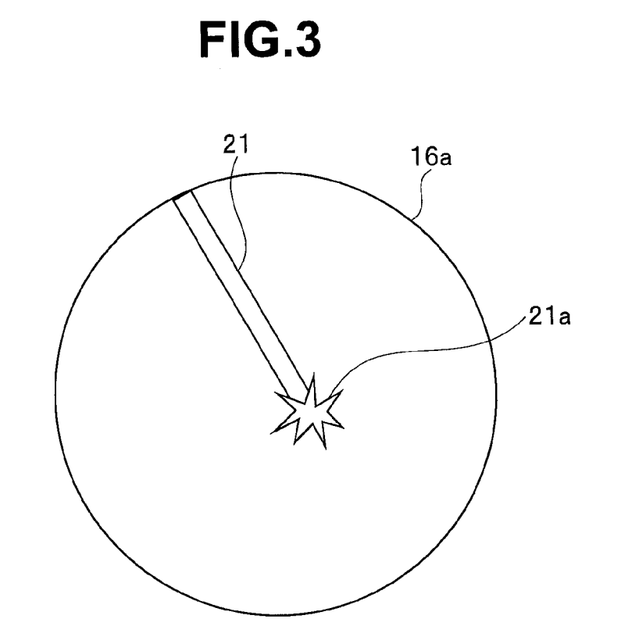
FIG. 3 is a diagram illustrating a state in which light generated by a treatment instrument exists within an observation view field in Embodiment 1.

Next, FIG. 3 is a diagram illustrating a state in which light generated by a treatment instrument 21 exists within the observation view field 16a.

When an examination is performed using the endoscope 6, the treatment instrument 21 may also be used. If the treatment instrument 21 is one provided to perform treatment of the subject, the treatment being accompanied by light emission, such as an electrosurgical knife or a therapeutic laser, as illustrated in FIG. 3, extrinsic light 21a (light that is not the return light of the illuminating light outputted from the optical fiber 3) is generated within the observation view field 16a. Furthermore, extrinsic light 21a may be generated for any reason that is not limited to the treatment instrument 21.

Figure 4:
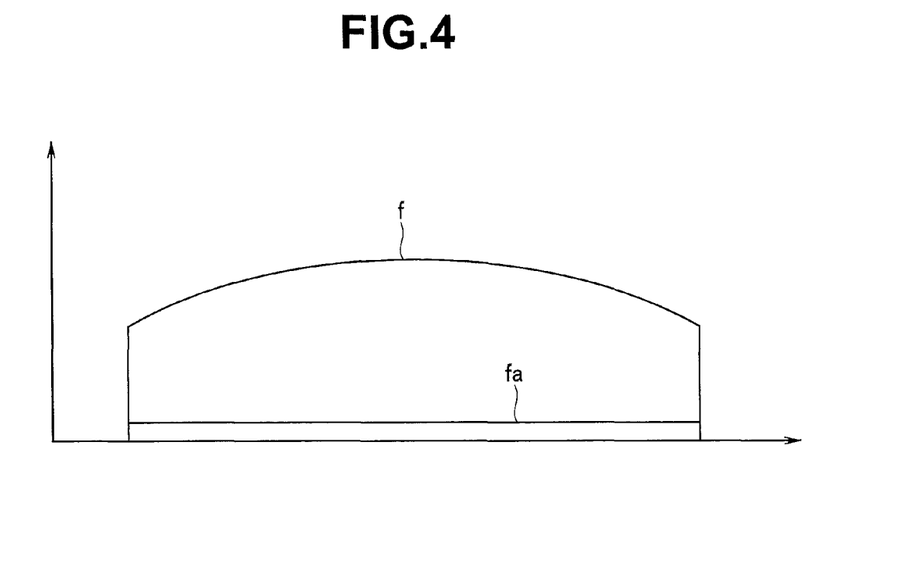
FIG. 4 is a diagram illustrating an example of a result of detection by a light detection section in Embodiment 1.

A state of a signal on one line, the signal being obtained in such a case as above, will be described with reference to FIG. 4. FIG. 4 is a diagram illustrating an example of a result of detection by the light detecting section 12.

If extrinsic light 21a exists within the observation view field 16a (that is, within the scanning range), the light detecting section 12 consistently detects the extrinsic light 21a regardless of the direction of scanning of the optical fiber 3. Accordingly, a detection signal f from the light detecting section 12 contains a signal component of return light of illumination light from the subject and a signal component fa of the extrinsic light 21a. Here, a signal value of the signal component of the return light varies depending on the reflectivity of the part of the subject to which the illuminating light is applied. On the other hand, the signal component fa of the extrinsic light 21a is constant as illustrated in FIG. 4 if a luminance level of the extrinsic light 21a is constant without, for example, temporal fluctuations.

Figure 5:
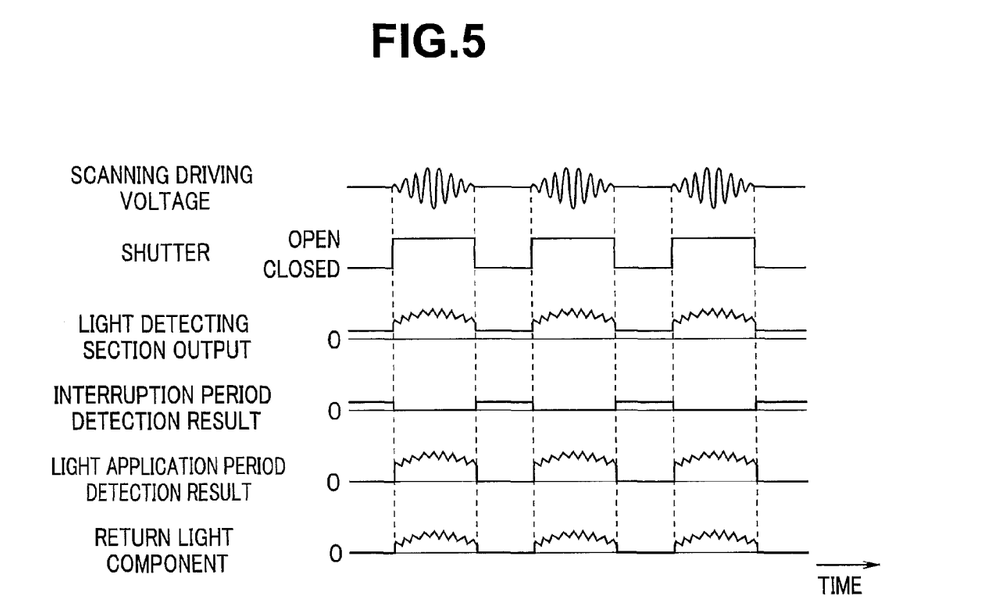
FIG. 5 is a timing chart indicating a scanning driving voltage, a shutter, a light detection section output and a return light component in Embodiment 1.

Next, FIG. 5 is a timing chart indicating a scanning driving voltage, a shutter, an output of the light detecting section 12 and a return light component.

A scanning driving voltage of a current supplied from the scanning drive section 8 to the drive element 7 has a waveform, for example, such as illustrated in FIG. 5. In the waveform, a point of start of fluctuations of an amplitude of the scanning driving voltage is a point where scanning is started from the center point A illustrated in FIG. 2, and a point where the amplitude of the scanning driving voltage has a largest value is a point where the scanning reaches the farthest point B illustrated in FIG. 2. Subsequently, scanning is returned to the center point A by following the spiral route from the farthest point B, and thus, the amplitude of the scanning driving voltage gradually decreases. Thus, an image for two frames is obtained while the amplitude of the scanning driving voltage reaches the largest value from zero and then returns to zero again. In a period in which the image for two frames is obtained, the shutter 4 is opened, that is, the period is a light application period in which illuminating light is applied from the distal end of the optical fiber 3.

After the light application period, an interruption period in which the application of the illuminating light from the distal end of the optical fiber 3 is interrupted comes, and during that period, the amplitude of the scanning driving voltage is zero.

The detection signal from the light detecting section 12 exhibits different waveforms in light application periods and interruption periods. In other hand, in the interruption periods, what is detected by the light detecting section 12 is the extrinsic light 21a. On the other hand, in the light application periods, what are detected by the light detecting section 12 are the return light and the extrinsic light 21a.

Therefore, the extrinsic light component removal section 13 acquires information indicating whether the present time is in a light application period or an interruption period, from the intermittent light output control section 5, and performs processing that differs depending on the acquired information.

Figure 6:
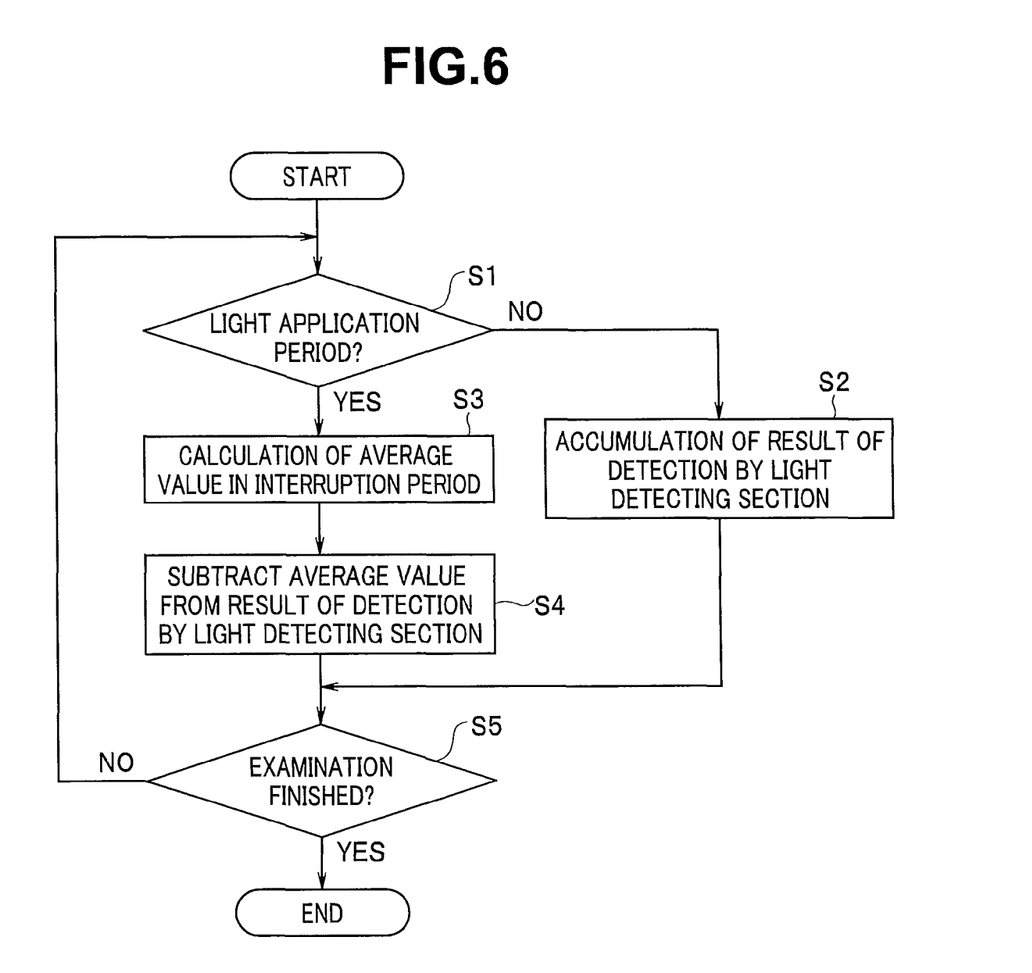
FIG. 6 is a flowchart illustrating processing in an extrinsic light component removal section in Embodiment 1.

FIG. 6 is a flowchart illustrating processing by the extrinsic light component removal section 13.

Upon start of the processing, the extrinsic light component removal section 13 determines whether the present time is in a light application period or an interruption period, based on the information acquired from the intermittent light output control section 5 (step S1).

Here, if it is determined that the present time is in an interruption period, the extrinsic light component removal section 13 accumulates a result of detection by the light detecting section 12 (see the interruption period detection result in FIG. 5) (step S2).

Then, whether or not the endoscopic examination has been finished is determined (step S5). Here, if the examination has not been finished, the processing returns to step S1 and the above determination is made.

If it is determined in step Si that the present time is in a light application period as described above, the extrinsic light component removal section 13 calculates an average value of the detection signal in the interruption period, which has been accumulated in step S2 (step S3).

Furthermore, the average value calculated in step S3 is subtracted, for example, in real time from a detection result that is being outputted from the light detecting section 12 in the light application period (see the light application period detection result in FIG. 5), to extract a return light component such as illustrated in FIG. 5, and the return light component is outputted to the image processing section 15 (step S4). In other words, the extrinsic light component removal section 13 subtracts an extrinsic light component obtained in an interruption period immediately before a light application period (here, specifically, an average value of the extrinsic light component) from a result of detection by the light detecting section 12, which has been obtained in the light application period, to remove the extrinsic light component.

Subsequently, in step S5, if it is determined that the endoscopic examination has been finished, the extrinsic light component removal section 13 terminates the processing.

According to Embodiment 1 described above, an extrinsic light component contained in a signal detected by the light detecting section 12 in a light application period is estimated based on extrinsic light 21a detected in an interruption period, and removed, whereby an effect of the extrinsic light 21a is reduced, enabling enhancement in quality of an image based on return light.

Here, since an extrinsic light component obtained in an interruption period immediately before a light application period is subtracted from a result of detection by the light detecting section 12 in the light application period, enabling highly-accurate extrinsic light component removal if temporal change of the extrinsic light component is small.

Furthermore, since an average value of an extrinsic light component in an interruption period is calculated, fluctuations and/or flickering in a short period of time are suppressed, enabling provision of stable removal performance.

[Embodiment 2]

Figure 7:
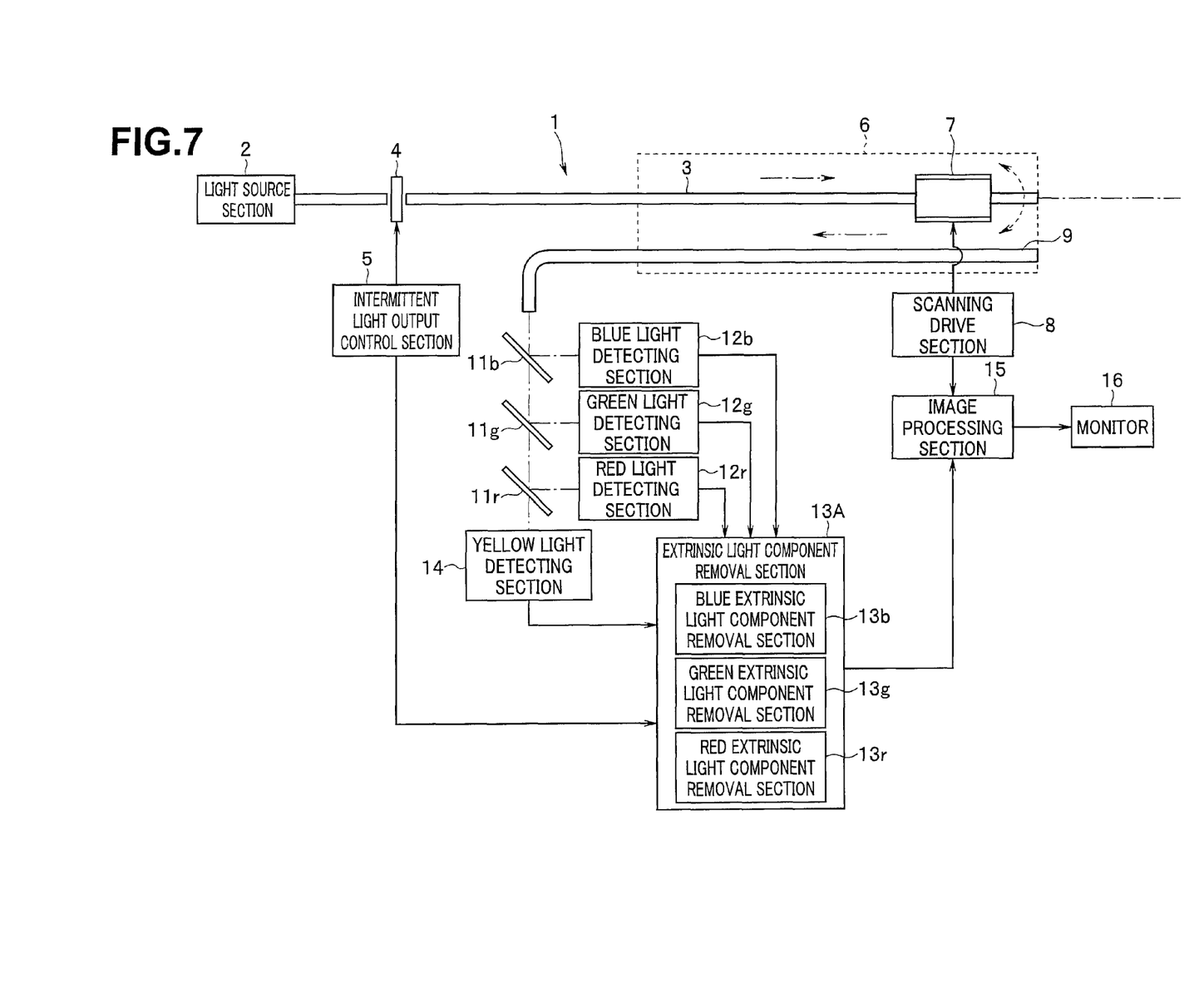
FIG. 7 is a diagram illustrating an example configuration of a scanning endoscope apparatus according to Embodiment 2 of the present invention.
Figure 8:
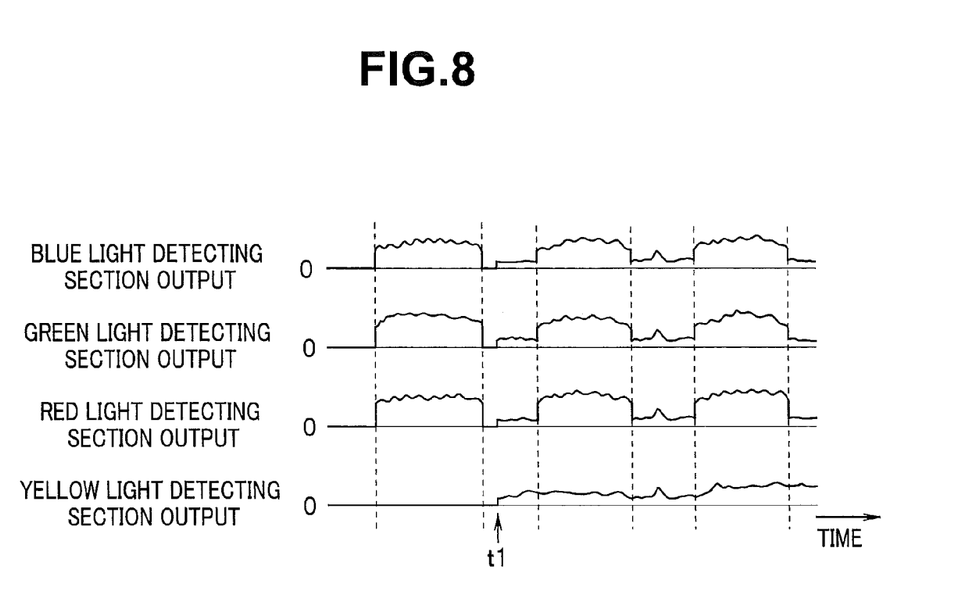
FIG. 8 is a timing chart illustrating respective outputs of blue, green, red and yellow light detecting sections in Embodiment 2.
Figure 9:
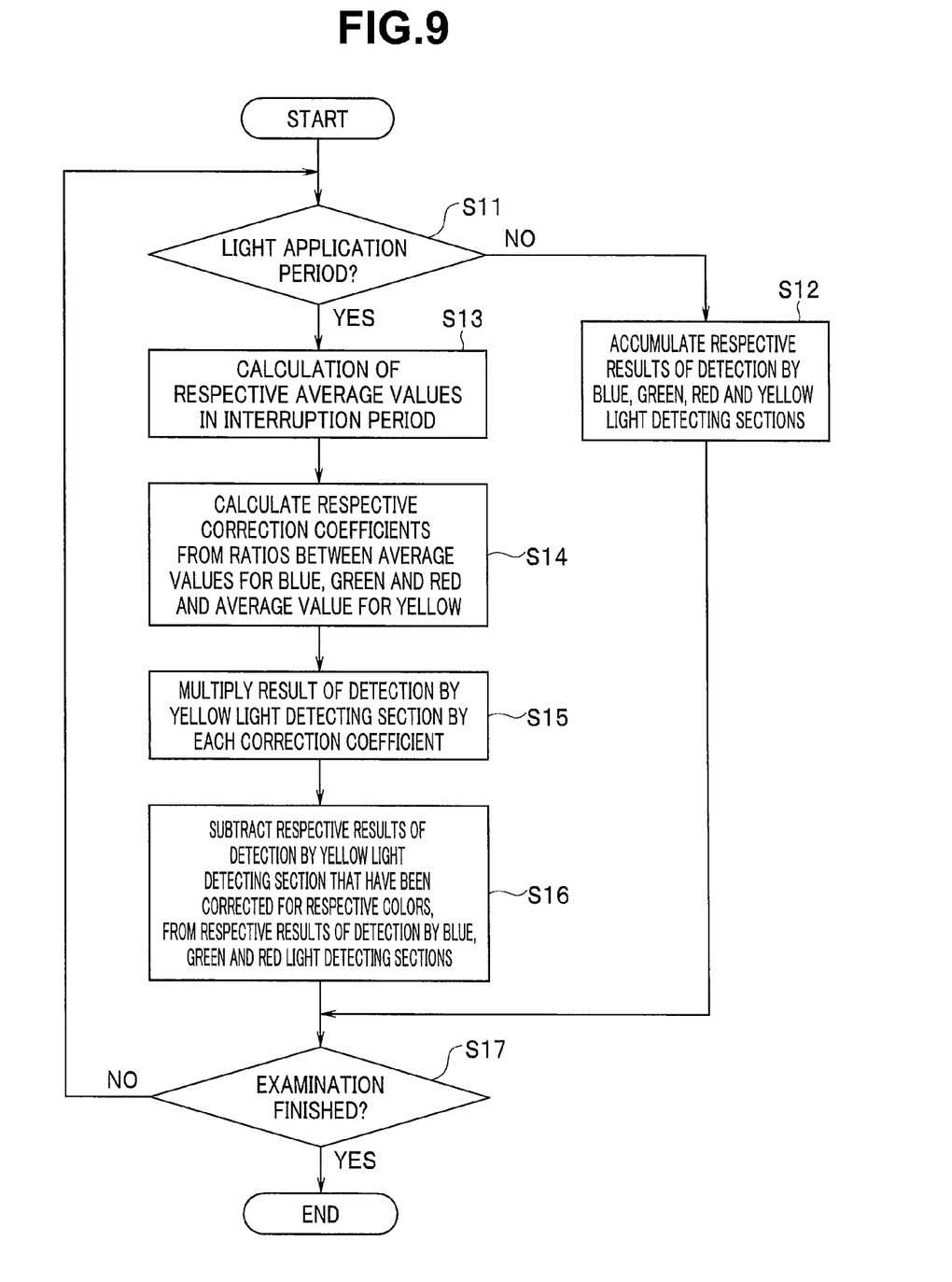
FIG. 9 is a flowchart illustrating processing in an extrinsic light component removal section in Embodiment 2.

FIGS. 7 to 9 are diagrams illustrating Embodiment 2 of the present invention, and FIG. 7 is a diagram illustrating an example configuration of a scanning endoscope apparatus 1. In Embodiment 2, a description of parts that are similar to those in Embodiment 1 described above will arbitrarily be omitted by, e.g., providing reference numerals that are the same as those in Embodiment 1 to the relevant parts, and points of difference will be mainly described.

In the present embodiment, an extrinsic light component is estimated for each of RGB color components in color illuminating light and the estimated extrinsic light components are removed.

First, the scanning endoscope apparatus 1 according to the present embodiment includes a blue light detecting section 12b, a green light detecting section 12g and a red light detecting section 12r.

In light outputted from a proximal end of an optical fiber bundle 9, only a narrow-band blue light component including a blue light band, which has been emitted from a blue light emitting laser in a light source section 2, is reflected by a blue light isolation mirror 11b, and components other than the blue light component are transmitted.

In the light that has passed through the blue light isolation minor 11b, only narrow-band green light component including a green light band, which has been emitted from a green light emitting laser in the light source section 2, is reflected by a green light isolation mirror 11g, and components other than the green light component are transmitted.

Furthermore, in light that has passed through the green light isolation minor 11g, only a narrow-band red light component including a red light band, which has been emitted from a red light emitting laser in the light source section 2, is reflected by a red light isolation mirror 11r, and components other than the red light component are transmitted.

As described above, the blue light detecting section 12b receives only a narrow-band blue light component, the green light detecting section 12g receives only a narrow-band green light component and the red light detecting section 12r receives only a narrow-band red light component, and in other words, the blue, green and red light detecting sections 12b, 12g and 12r detect light in respective wavelength bands of a plurality of colors in illuminating light of the plurality of colors.

Although not described in detail above, the above-described light detecting section 12 according to Embodiment 1 is configured generally similar to the above.

Also, the light that has passed through the red light isolation mirror 11r contains a light component other than the narrow-band blue light component, the narrow-band green light component and the narrow-band red light component, which have been removed (the light component is referred to as "yellow light component" below). On an optical path of the light transmitted by the red light isolation minor 11r, a yellow light detecting section 14 that detects a yellow light component is arranged. In other words, the yellow light detecting section 14 is a second light detecting section that does not detect light in any of wavelength bands of the aforementioned plurality of colors in illuminating light, but detects light in a wavelength band other than the wavelength bands of the plurality of colors in the illuminating light.

FIG. 8 is a timing chart indicating respective outputs of the blue light detecting section 12b, the green light detecting section 12g, the red light detecting section 12r and the yellow light detecting section 14. FIG. 8 indicates a state in which extrinsic light 21a is generated at a time t1 onwards.

Up to the time t1, only return light components exist, and thus, the blue light detecting section 12b, the green light detecting section 12g and the red light detecting section 12r detect and output return light in a light application period, but the outputs are zero in an interruption period. Also, the yellow light detecting section 14 detects no respective color components contained in illuminating light, and thus, the output is zero in both of the light application period and the interruption period.

At the time t1 onwards, light entering the optical fiber bundle 9 contains a return light component and an extrinsic light component. If the extrinsic light component is a component with a relatively-wide band, which can be detected by any of the blue light detecting section 12b, the green light detecting section 12g, the red light detecting section 12r and the yellow light detecting section 14, as illustrated in FIG. 8, the extrinsic light component is outputted from the yellow light detecting section 14, and the extrinsic light component output is superimposed on return light component outputs from the other blue light, green light and red light detecting sections 12b, 12g and 12r.

These results of detection by the blue light detecting section 12b, the green light detecting section 12g, the red light detecting section 12r and the yellow light detecting section 14 are inputted to an extrinsic light component removal section 13A. The extrinsic light component removal section 13A removes the extrinsic light components for the respective color components, based on the inputted respective detection results and information indicating whether the present time is in a light application period or an interruption period, the information being acquired from the intermittent light output control section 5.

In other words, the extrinsic light component removal section 13A includes a blue extrinsic light component removal section 13b, a green extrinsic light component removal section 13g and a red extrinsic light component removal section 13r.

The blue extrinsic light component removal section 13b removes the blue extrinsic light component from the result of detection by the blue light detecting section 12b, based on the information acquired from the intermittent light output control section 5 and the result of detection by the yellow light detecting section 14.

The green extrinsic light component removal section 13g removes the green extrinsic light component from the result of detection by the green light detecting section 12g, based on the information acquired from the intermittent light output control section 5 and the result of detection by the yellow light detecting section 14.

The red extrinsic light component removal section 13r removes the red extrinsic light component from the result of detection by the red light detecting section 12r, based on the information acquired from the intermittent light output control section 5 and the result of detection by the yellow light detecting section 14.

FIG. 9 is a flowchart illustrating processing in the extrinsic light component removal section 13A.

Upon start of the processing, the extrinsic light component removal section 13A determines whether the present time is in a light application period or an interruption period, based on information acquired from the intermittent light output control section 5 (step S11).

Here, if it is determined that the present time is in an interruption period, the extrinsic light component removal section 13A accumulates results of detection by the blue light detecting section 12b, the green light detecting section 12g, the red light detecting section 12r and the yellow light detecting section 14, respectively (step S12).

Then, whether or not the endoscopic examination has been finished is determined (step S17). If the examination has not been finished, the processing returns to step S11 and the above-described determination is made.

Then, if it is determined in step S11 that the present time is in a light application period, the extrinsic light component removal section 13A calculates an average value of each of the detection signals in the interruption period, which has been accumulated in step S12 (step S13). More specifically, the extrinsic light component removal section 13A calculates an average value Yave of the detection signal from the yellow light detecting section 14, the blue extrinsic light component removal section 13b calculates an average value Bave of the detection signal from the blue light detecting section 12b, the green extrinsic light component removal section 13g calculates an average value Gave of the detection signal from the green light detecting section 12g, and the red extrinsic light component removal section 13r calculates an average value Rave of the detection signal from the red light detecting section 12r, respectively.

Here, the average value Yave represents an average intensity of the extrinsic light component of yellow light in the interruption period, the average value Bave represents an average intensity of the extrinsic light component of blue light in the interruption period, the average value Gave represents an average intensity of the extrinsic light component of green light in the interruption period, and the average value Rave represents an average intensity of the extrinsic light component of red light in the interruption period, respectively.

Next, the blue extrinsic light component removal section 13b calculates a correction coefficient $\alpha b$ based on the average values Yave and Bave, the green extrinsic light component removal section 13g calculates a correction coefficient $\alpha g$ based on the respective average values Yave and Gave, and the red extrinsic light component removal section 13r calculates a correction coefficient $\alpha r$ based on the respective average values Yave and Rave, respectively, according to, for example, Expression 1 below (step S14).

$$\alpha b = Bave/Yave$$

$$\alpha g = Gave/Yave$$

$$\alpha r = Rave/Yave \qquad \text{Expression 1}$$

Here, the correction coefficient αb is a coefficient for transforming the intensity of the extrinsic light component of yellow light into an intensity of an extrinsic light component of blue light, the correction coefficient αg is a coefficient for transforming the intensity of the extrinsic light component of yellow light into an intensity of an extrinsic light component of green light, and the correction coefficient αr is a coefficient for transforming the intensity of the extrinsic light component of yellow light into an intensity of an extrinsic light component of red light.

Subsequently, the blue extrinsic light component removal section 13b multiplies a detection signal Y(t) that is being detected in real time by the yellow light detecting section 14 in the light application period, by the correction coefficient αb to calculate an estimated extrinsic light component αb×Y(t) contained in real time in a detection signal from the blue light detecting section 12b, the green extrinsic light component removal section 13g multiplies the detection signal Y(t) by the correction coefficient αg to calculate an estimated extrinsic light component αg×Y(t) contained in real time in the green light detecting section 12g, and the red extrinsic light component removal section 13r multiplies the detection signal Y(t) by the correction coefficient αr to calculate an estimated extrinsic light component αr×Y(t) contained in real time in the red light detecting section 12r (step S15).

Then, the blue extrinsic light component removal section 13b subtracts the extrinsic light component αb×Y(t) from a detection signal B(t) that is being detected in real time by the blue light detecting section 12b in the light application period, the green extrinsic light component removal section 13g subtracts the extrinsic light component αg×Y(t) from a detection signal G(t) that is being detected in real time by the green light detecting section 12g in the light application period, and the red extrinsic light component removal section 13r subtracts the extrinsic light component αr×Y(t) from a detection signal R(t) that is being detected in real time by the red light detecting section 12r in the light application period, to calculate a real-time blue return light component Bret(t), a real-time green return light component Gret(t) and a real-time red return light component Rret(t) as indicated in Expression 2 below (step S16).

$$Bret(t) = B(t) - \alpha b \times Y(t)$$

$$Gret(t) = G(t) - \alpha g \times Y(t)$$

$$Rret(t) = R(t) - \alpha r \times Y(t) \qquad \text{Expression 2}$$

Subsequently, the processing advances to step S17, and whether or not the endoscopic examination has been finished is determined in such a manner as described above. Here, if it is determined that the endoscopic examination has been finished, the extrinsic light component removal section 13A terminates the processing.

According to Embodiment 2 described above, effects that are almost similar to those of Embodiment 1 can be provided, and a result of detection by the yellow light detecting section 14 in a light application period is corrected based on a ratio of each of results of detection by the blue light detecting section 12b, the green light detecting section 12g and the red light detecting section 12r relative to the result of detection by the yellow light detecting section 14 in an interruption period, to estimate an extrinsic light component contained in each of respective results of detection by the blue light detecting section 12b, the green light detecting section 12g and the red light detecting section 12r in a light application period, enabling real-time estimation of extrinsic light components. As a result, the extrinsic light components can be removed in real time, enabling extraction of return light components of illuminating light from a subject.

Furthermore, estimation of extrinsic light components contained in blue light, green light and red light is performed for the respective colors, enabling extrinsic light component removal that is more suitable for each color component.

Note that, although the above description has been provided mainly in terms of scanning endoscope apparatuses, the present invention may be applied to an image processing apparatus that processes an image obtained from a scanning endoscope apparatus in such a manner as described above, or an image processing method, or a control program for making a computer control a scanning endoscope apparatus or an image processing apparatus in such a manner as described above or a computer-readable recording medium or the like that records the control program therein.

In particular, for example, if an image processing apparatus corresponding to Embodiment 1 described above is formed, arrangement may be made so that the image processing apparatus includes an extrinsic light component removal section 13 and an image processing section 15 to process an image obtained by an scanning endoscope apparatus including a light source section 2, an optical fiber 3, a shutter 4 and an intermittent light output control section 5, a drive element 7 and a scanning drive section 8 and a light detecting section 12. Also, an idea similar to the above can be applied to a case where an image processing apparatus corresponding to Embodiment 2 described above is formed.

The present invention is not limited to the above-described embodiments as they are, but can be embodied with the components modified without departing from the spirit of the present invention in the practical phase. A proper combination of a plurality of components disclosed in the above-described embodiments enables formation of any of various aspects of the invention. For example, some components may be deleted from all the components indicated in the embodiments. Furthermore, components in different embodiments may arbitrarily be combined. As described above, it should be understood that various modifications and applications are possible without departing from the spirit of the invention.

What is claimed is:

1. A scanning endoscope apparatus comprising:
    a light source section that emits illuminating light;
    a light guiding section that guides and applies the illuminating light to a subject from a distal end in such a manner that the illuminating light has directionality;
    a scanning section that performs scanning in which a direction of the distal end of the light guiding section is varied;
    a first light detecting section that detects light in a wavelength band of the illuminating light;
    a second light detecting section that does not detect light in the wavelength band of the illuminating light, but detects light in a wavelength band other than the wavelength band of the illuminating light;
    an illumination control section that controls a light application period in which the illuminating light is applied from the distal end of the light guiding section and an interruption period in which the application of the illuminating light from the distal end of the light guiding section is interrupted;

a removal section that corrects a result of detection by the second light detecting section in the light application period, based on a ratio of a result of detection by the first light detecting section relative to a result of detection by the second light detecting section in the interruption period to estimate an extrinsic light component contained in the result of detection by the first light detecting section in the light application period, and removes the estimated extrinsic light component to extract a return light component of the illuminating light from the subject; and an image processing section that forms image information to be outputted to a display section that displays an image, based on the return light component extracted by the removal section.

2. The scanning endoscope apparatus according to claim 1, wherein the light source section emits illuminating light of a plurality of colors;

wherein the first light detecting section detects light in a wavelength band of each of the plurality of colors from the illuminating light of the plurality of colors;

wherein the second light detecting section detects light in a wavelength band other than the wavelength bands of the illuminating light of the plurality of colors; and wherein the removal section estimates the extrinsic light component contained in the result of detection by the first light detecting section, for an illuminating light component of each of the plurality of colors and removes the extrinsic light component estimated for the illuminating light component of each of the plurality of colors.

* * * * *